US012262957B2

United States Patent
Chen et al.

(10) Patent No.: US 12,262,957 B2
(45) Date of Patent: Apr. 1, 2025

(54) SYSTEM AND METHOD FOR POSITION AND POSTURE DETECTION OF SURGICAL MACHINE

(71) Applicant: METAL INDUSTRIES RESEARCH & DEVELOPMENT CENTRE, Kaohsiung (TW)

(72) Inventors: Ming-Hui Chen, Kaohsiung (TW); Hsien-Ju Wu, Kaohsiung (TW); Kai-Szu Lo, Tainan (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 721 days.

(21) Appl. No.: 17/558,715

(22) Filed: Dec. 22, 2021

(65) Prior Publication Data
US 2023/0190384 A1 Jun. 22, 2023

(51) Int. Cl.
*A61B 34/20* (2016.01)
*A61B 90/00* (2016.01)

(52) U.S. Cl.
CPC .............. *A61B 34/20* (2016.02); *A61B 90/06* (2016.02); *A61B 90/39* (2016.02); *A61B 2034/2068* (2016.02); *A61B 2034/2072* (2016.02); *A61B 2090/067* (2016.02)

(58) Field of Classification Search
CPC .... A61B 2034/2055; A61B 2034/2057; A61B 2034/2068; A61B 2034/2059; A61B 2034/2072; A61B 2090/3983; A61B 2090/3995; A61B 2090/067; A61B 34/20; A61B 90/39
See application file for complete search history.

(56) References Cited

U.S. PATENT DOCUMENTS

2019/0328462 A1* 10/2019 Liu .................. G16H 40/63

FOREIGN PATENT DOCUMENTS

CN 213430521 U 6/2021

OTHER PUBLICATIONS

Taiwanese Office Action mailed Apr. 11, 2022 for Taiwanese Patent Application No. 110141574, 7 pages.

* cited by examiner

*Primary Examiner* — Majid Jamialahmadi
(74) *Attorney, Agent, or Firm* — Demian K. Jackson; Jackson IPG PLLC

(57) ABSTRACT

System and method for position and posture detection are provided to determine whether to update an original position and posture information of a surgical machine during surgery navigation. The system includes a sensing element, a displacement and/or angle sensing element and a processor. A coordinate signal of a marker module generated by the sensing element and a displacement and/or angle signal of the marker module generated by the displacement and/or angle sensing element are received by the processor and used to create a transformation matrix. A position and posture information of the surgical machine is obtained using the transformation matrix and the coordinate signal and provided to determine whether to update the original position and posture information.

13 Claims, 4 Drawing Sheets

SYSTEM AND METHOD FOR POSITION AND POSTURE DETECTION OF SURGICAL MACHINE

FIELD OF THE INVENTION

This invention relates to a system and method for position and posture detection which is provided to inspect whether original position and posture information of a surgical machine used in surgery is required to be updated for surgery navigation.

BACKGROUND OF THE INVENTION

Conventionally, an original position and posture information of surgical machine, such as robotic arm or carrier, needs to be set up in a surgery navigation system before surgery such that a surgical instrument, for example, surgical drill, bone breaking tool, bone anchor, clamp or bone screw instrumentation, can be operated according to the original position and posture information during surgery navigation.

The surgical machine is positioned by a sensor which is provided to sense a marker module mounted on the surgical machine. However, user who operates the surgical machine needs to be careful to avoid blocking a sensing path of the sensor to sense a marker of the marker module, that causes inconvenience to user.

The surgical machine and/or the marker module can be moved to change the sensing path of the sensor to avoid blocking the sensing path, but the surgery navigation system cannot know that the surgical machine and/or the marker module are moved and cannot know whether position and posture information of the surgical machine is different to the original and stored one after the surgical machine and/or the marker module are moved. Thus, moving the surgical machine and/or the marker module may increase length of time required for surgery navigation and decrease accuracy of surgery navigation.

SUMMARY

One object of the present invention is to provide a system and method for position and posture detection to know whether a position and posture information of a surgical machine is required to be updated after changing position or posture of the surgical machine and/or a marker module mounted on the surgical machine during surgery. The system and method can improve accuracy of surgery navigation.

A system for position and posture detection of the present invention is provided to determine whether to update an original position and posture information of a surgical machine stored in a surgery navigation system after the surgical machine and/or a marker module mounted on the surgical machine is moved during surgery. The system includes a sensing element, a displacement and/or angle sensing element and a processor. The sensing element is provided to sense a marker of the marker module to generate a coordinate signal, the displacement and/or angle sensing element is provided to sense the marker module to generate a displacement and/or angle signal, and the processor is provided to receive the coordinate signal and the displacement and/or angle signal. As the coordinate signal received by the processor is different to an original coordinate signal of the marker, the processor creates a transformation matrix according to the displacement and/or angle signal and generates a position and posture information of the surgical machine using the transformation matrix and the coordinate signal. The obtained position and posture information can be used to determine whether to update the original position and posture information.

A method for position and posture detection of the present invention is provided to determine an original position and posture information of a surgical machine stored in a surgery navigation system is required to be updated or not after the surgical machine and/or a marker module mounted on the surgical machine is moved during surgery. The method includes the steps as follows. Sensing a marker of the marker module to generate a coordinate signal using a sensing element, sensing the marker module to generate a displacement and/or angle signal using a displacement and/or angle sensing element, and receiving the coordinate signal and the displacement and/or angle signal using a processor. While the coordinate signal received by the processor is different to an original coordinate signal of the marker, the processor creates a transformation matrix according to the displacement and/or angle signal and generates a position and posture information of the surgical machine using the transformation matrix and the coordinate signal. The obtained position and posture information can be used to determine whether to update the original position and posture information.

In the present invention, the position and posture information of the surgical machine calculated using the transformation matrix and the coordinate signal is provided to determine whether the original position and posture information is required to be adjusted such that it is possible to increase accuracy of the surgery navigation system. Accordingly, accuracy and success rate of surgery can be enhanced.

DETAILED DESCRIPTION OF THE INVENTION

Figure 1:
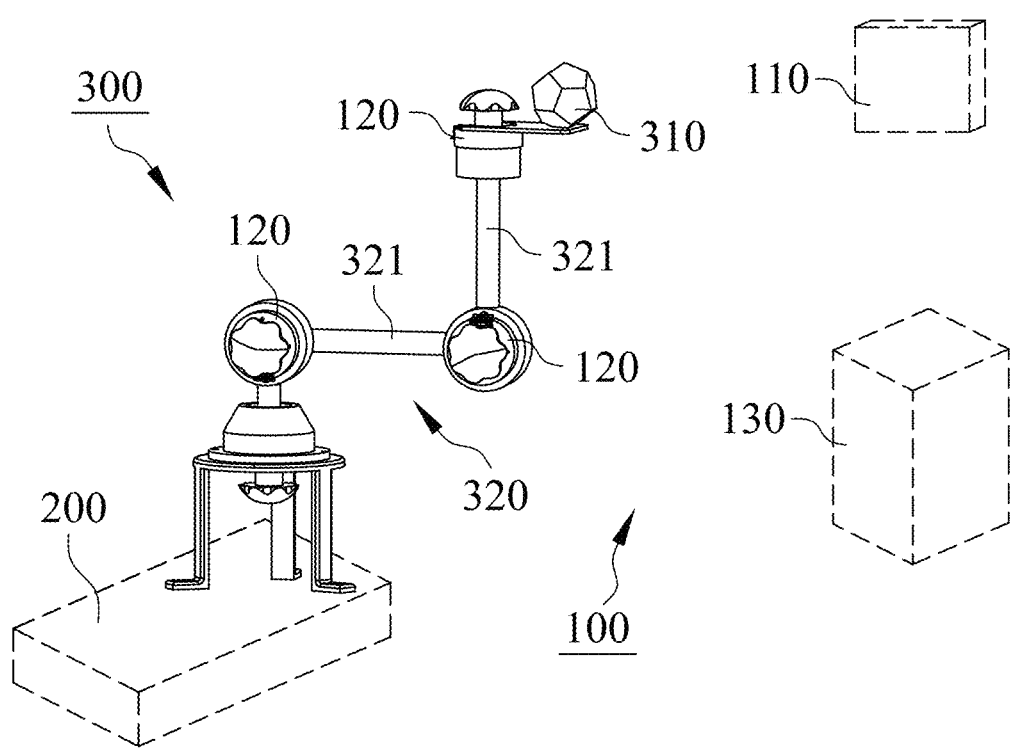
FIG. 1 is a perspective assembly diagram illustrating a surgical machine in an original state and a system for position and posture detection in accordance with one embodiment of the present invention.
Figure 2:
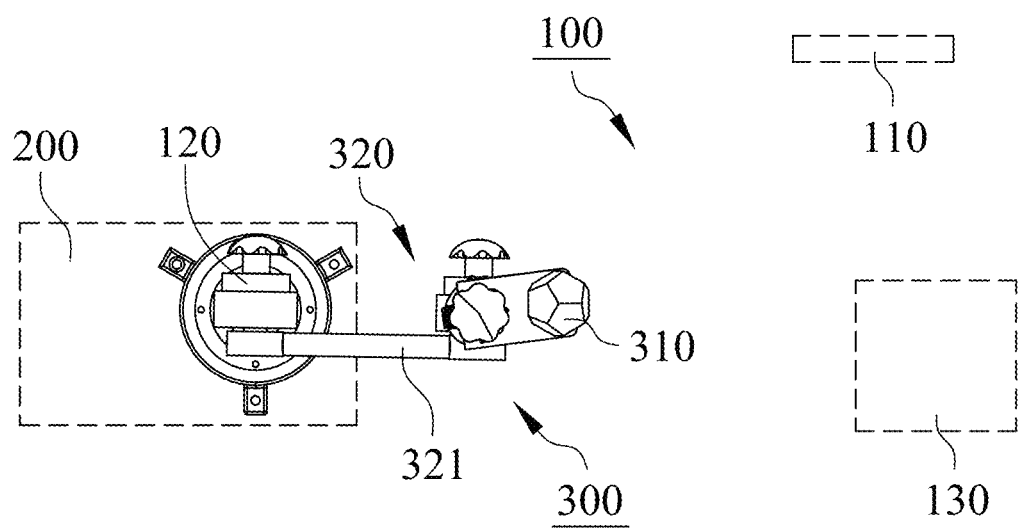
FIG. 2 is a top view diagram illustrating the surgical machine in an original state and the system for position and posture detection in accordance with one embodiment of the present invention.

With reference to FIGS. 1 and 2, before surgery, a surgical machine 200 is positioned in an original position and posture and its original position and posture information is stored in a surgery navigation system (not shown). The surgical machine 200 may be robotic arm or robotic carrier. The original position and posture information is necessary for a surgical instrument, such as surgical drill, bone breaking tool, bone anchor, clamp or bone screw instrumentation, during surgery navigation.

With reference to FIGS. 1 and 2, if the surgical machine 200 and/or a marker module 300 mounted on the surgical machine 200 is moved or changed to another posture, a system for position and posture detection 100 of the present invention can be provided to determine whether the original position and posture information of the surgical machine 200 is required to be updated for surgery navigation.

With reference to FIGS. 1 and 2, before moving the surgical machine 200 and/or the marker module 300 mounted on the surgical machine 200 or changing its posture, the surgical machine 200 is located at a first position and the marker module 300 is fix in a first posture. After the surgical machine 200 and/or the marker module 300 mounted on the surgical machine 200 is moved or changed to another posture, a position and posture information regarding the surgical machine 200 is generated by the system 100 and used as reference to determine whether to update the original position and posture information.

With reference to FIGS. 1 and 2, the system 100 includes a sensing element 110, a displacement and/or angle sensing element 120 and a processor 130. The sensing element 110 is provided to sense a marker 310 of the marker module 300 and generate a coordinate signal including coordinate information of the marker 310. The marker 310 may be a light emitting element, a light sensor or a radio frequency device. The displacement and/or angle sensing element 120 is provided to sense the marker module 300 and generate a displacement and/or angle signal including displacement and/or angle information of the marker module 300. The displacement and/or angle sensing element 120 may be displacement encoder and/or angle encoder.

With reference to FIGS. 1 and 2, before changing the position or posture of the marker module 300, the sensing element 110 senses the marker 310 of the marker module 300 to generate an original coordinate signal, and the displacement and/or angle sensing element 120 senses the marker module 300 to generate an original displacement and/or angle signal. When the position or posture of the surgical machine 200 and/or the maker module 300 mounted on the surgical machine 200 is changed, the sensing element 110 senses the marker 310 to generate a coordinate signal in response to the moved marker 310. In this embodiment, the marker module 300 further includes a linkage mechanism 320, the marker 310 is mounted on the linkage mechanism 320, and the displacement and/or angle sensing element 120 is mounted between two links 321 of the linkage mechanism 320. While the posture of the linkage mechanism 320 is changed, the displacement and/or angle sensing element 120 can sense the linkage mechanism 320 to generate a displacement and/or angle signal regarding the linkage mechanism 320.

With reference to FIGS. 1 and 2, the processor 130 can receive the coordinate signal and the displacement and/or angle signal. If the coordinate information in the coordinate signal is different to that in the original coordinate signal, the displacement and/or angle information in the displacement and/or angle signal is applied to an algorithm to create a transformation matrix, and the coordinate information in the coordinate signal is applied to the transformation matrix to obtain the position and posture information of the surgical machine 200 in the processor 130. According to the obtained position and posture information, it is possible to make a decision whether the original position and posture information should be replaced or not.

A method for position and posture detection of the surgical machine 200 using the system 100 is shown in FIGS. 1 to 8 and illustrated as follows.

With reference to FIGS. 1 and 2, the original position and posture information of the surgical machine 200, the original coordinate information of the marker 310 and the original displacement and/or angle information of the marker module 300 are input to a surgery navigation system (not shown) before surgical operation.

Figure 3:
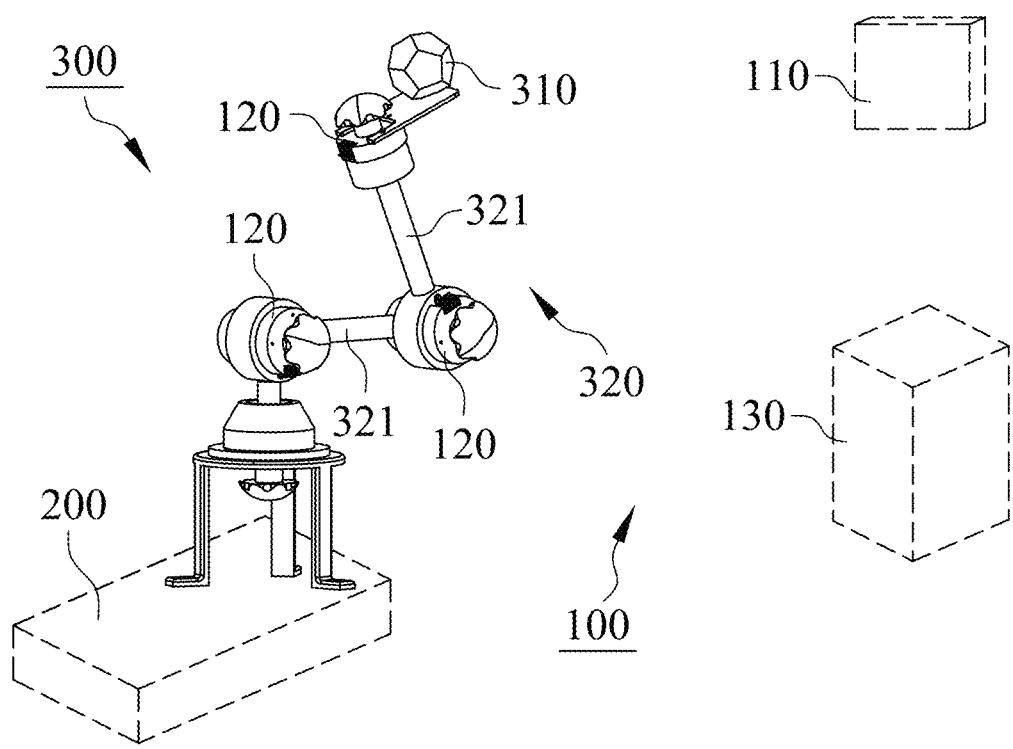
FIG. 3 is a perspective assembly diagram illustrating the surgical machine in a first state and the system for position and posture detection in accordance with one embodiment of the present invention.
Figure 4:
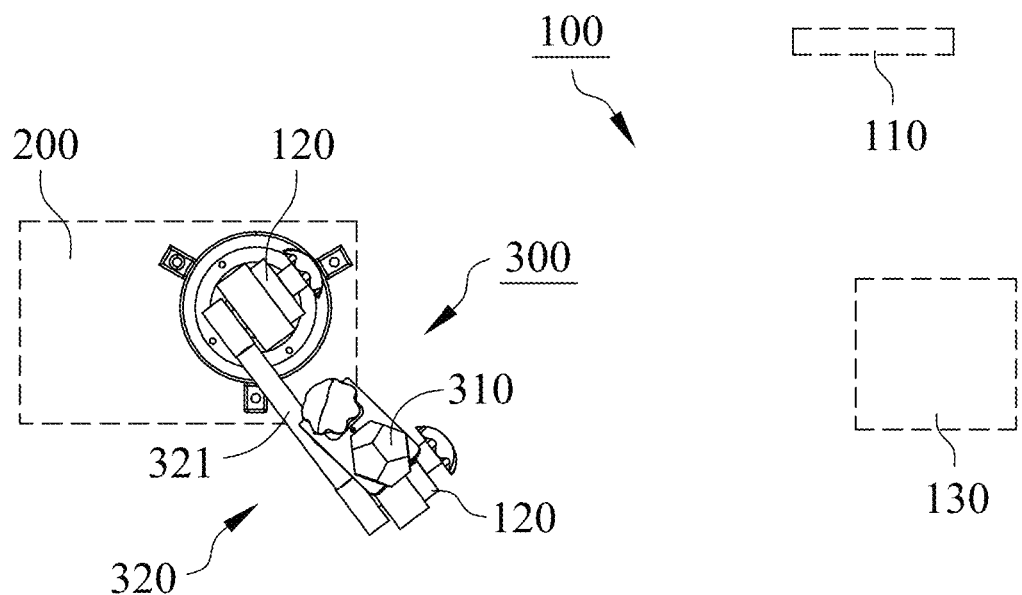
FIG. 4 is a top view diagram illustrating the surgical machine in a first state and the system for position and posture detection in accordance with one embodiment of the present invention.

The surgical machine 200 in a first state during surgery is shown in FIGS. 3 and 4. In the first state, the position and posture of the surgical machine 200 is not changed, it is still located at the first position and in the original posture. Only the posture of the marker module 300 is changed from the first posture (as shown in FIGS. 1 and 2) to a second posture (as shown in FIGS. 3 and 4). The posture of the linkage mechanism 320 is changed to move the marker 310 by changing the included angle between the two links 321 of the linkage mechanism 320 or turning the linkage mechanism 320.

With reference to FIGS. 3 and 4, as the marker module 300 is arranged to the second posture, the sensing element 110 senses the marker 310 of the marker module 300 to generate a coordinate signal, the displacement and/or angle sensing element 120 senses the marker module 300 to generate a displacement and/or angle signal, and the processor 130 receives the coordinate signal and the displacement and/or angle signal. Because of the posture change of the marker 310, the coordinate signal corresponding to the marker 310 is different to the original coordinate signal such that a transformation matrix is determined based on the information in the displacement and/or angle signal. In this embodiment, a controller of auxiliary positioning module (not shown) is provided to form the transformation matrix according to the displacement and/or angle signal.

With reference to FIGS. 3 and 4, in this embodiment, the posture of the linkage mechanism 320 is changed from the first posture to the second posture so as to generate a displacement and/or angle signal different to the original one. Owing to the information in the displacement and/or angle signal and the original displacement and/or angle signal are not the same, a position and posture information of the surgical machine 200 related to posture change of the linkage mechanism 320 can be obtained by using the transformation matrix and the coordinate signal, and the system 100 can utilize the position and posture information to determine whether to update the original position and posture information.

With reference to FIGS. 3 and 4, in this embodiment, the position and posture information of the surgical machine 200 obtained using the transformation matrix with the coordinate signal is identical to the original position and posture information so the original position and posture information is not required to be updated for surgery navigation.

Figure 5:
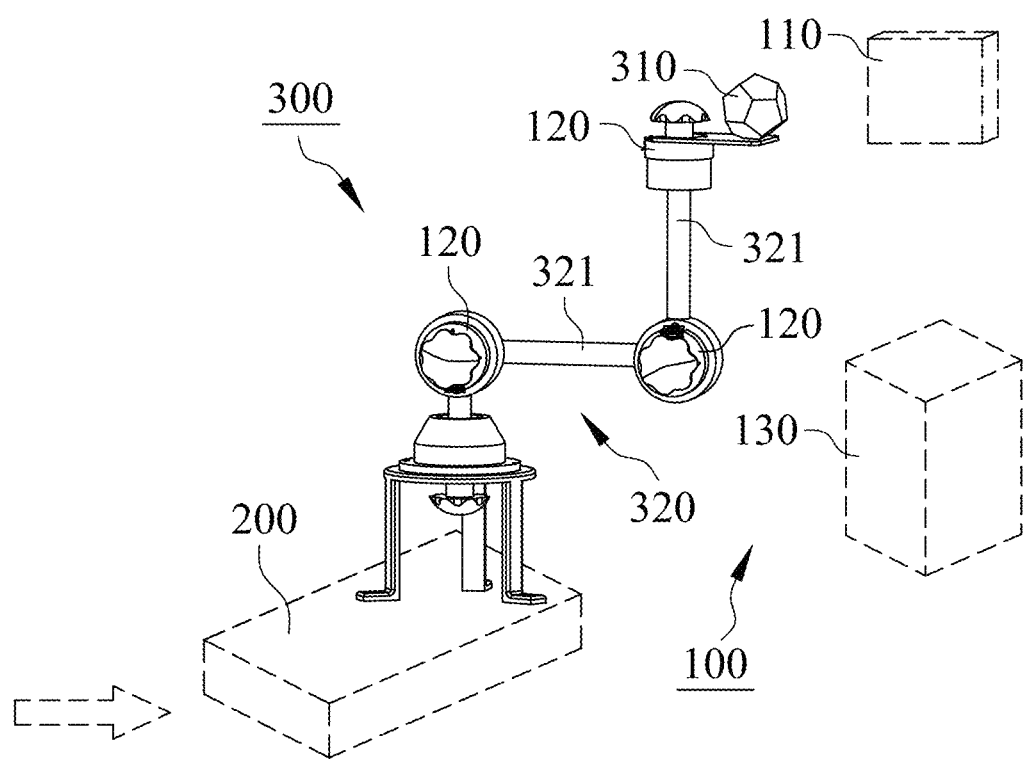
FIG. 5 is a perspective assembly diagram illustrating the surgical machine in a second state and the system for position and posture detection in accordance with one embodiment of the present invention.
Figure 6:
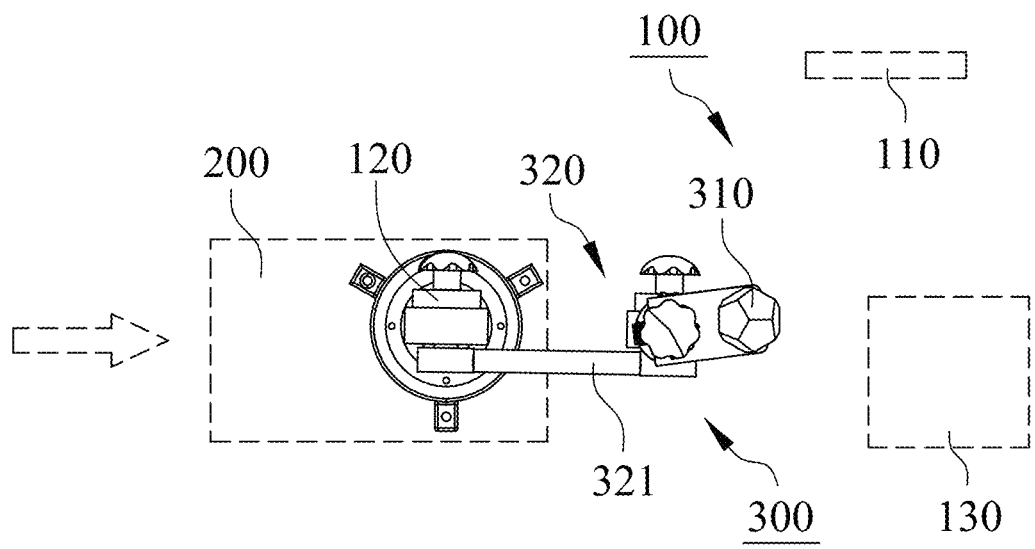
FIG. 6 is a top view diagram illustrating the surgical machine in a second state and the system for position and posture detection in accordance with one embodiment of the present invention.

The surgical machine 200 in a second state during surgery is shown in FIGS. 5 and 6. The surgical machine 200 is moved to change its position and/or posture, and the marker module 300 is not moved and kept in the first posture as shown in FIGS. 1 and 2. In the second state, the surgical machine 200 is moved from the first position as shown in FIGS. 1 and 2 to a second position as shown in FIGS. 5 and 6. In different states, the posture of the surgical machine 200 may be changed (e.g. changing the posture of the robotic arm of the surgical machine 200), and the position and posture of the surgical machine 200 may be both changed.

With reference to FIGS. 5 and 6, after moving the surgical machine 200 from the first position to the second position, the sensing element 110 senses the marker 310 of the marker module 300 to generate a coordinate signal, the displacement and/or angle sensing element 120 senses the marker module 300 to generate a displacement and/or angle signal, and the processor 130 receives the coordinate signal and the displacement and/or angle signal. In the second state, the displacement and/or angle signal is identical to the original displacement and/or angle signal owing to the posture of the marker module 300 is not altered, but the coordinate signal regarding the marker 310 is different to the original coordinate signal because the surgical machine 200 is moved. The processor 130 utilizes the information in the displacement and/or angle signal to create a transformation matrix as the coordinate signal is different to the original one.

With reference to FIGS. 5 and 6, only the surgical machine 200 is moved, the displacement and/or angle signal of the marker module 300 generated by the displacement and/or angle sensing element 120 is identical to the original displacement and/or angle signal, so a position and posture information obtained from the same transformation matrix and different coordinate signal is not identical to the original position and posture information. Thus, the original position and posture information has to be updated.

Figure 7:
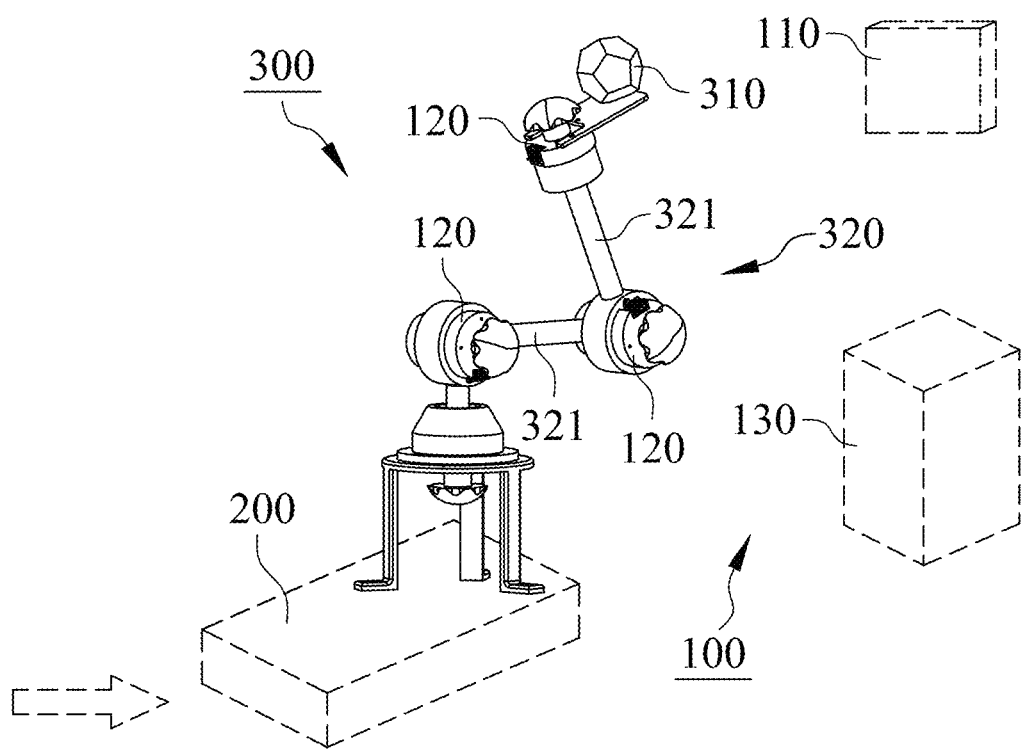
FIG. 7 is a perspective assembly diagram illustrating the surgical machine in a third state and the system for position and posture detection in accordance with one embodiment of the present invention.
Figure 8:
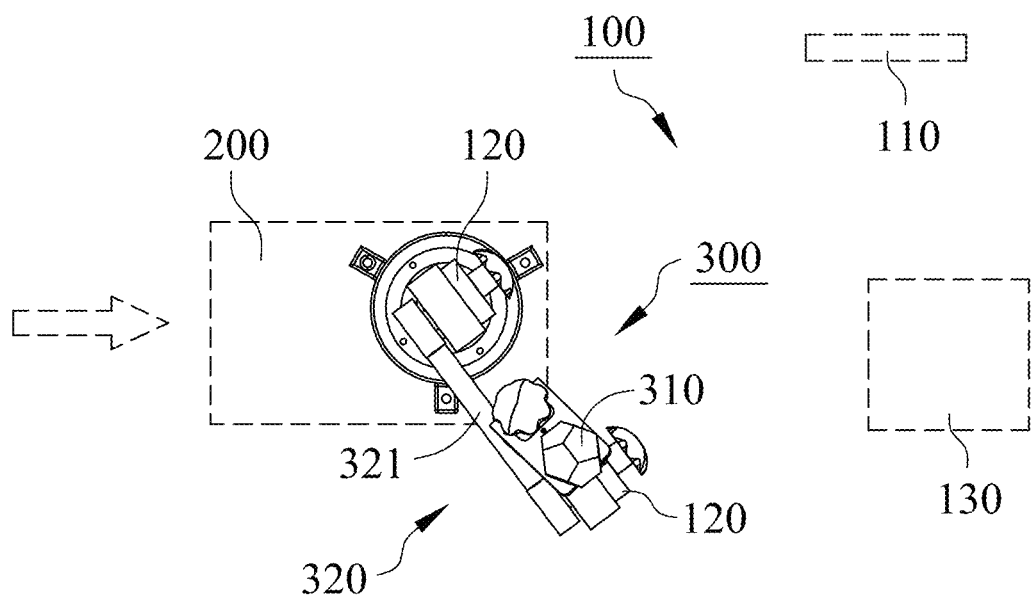
FIG. 8 is a top view diagram illustrating the surgical machine in a third state and the system for position and posture detection in accordance with one embodiment of the present invention.

FIGS. 7 and 8 show the surgical machine 200 of a third state during surgery. The position and/or posture of the surgical machine 200 and the posture of the marker module 300 can be both changed. In the third state, the surgical machine 200 is moved from the first position as shown in FIGS. 1 and 2 to a second position as shown in FIGS. 7 and 8, and the maker module 300 is changed from the first posture as shown in FIGS. 1 and 2 to a second posture as shown in FIGS. 7 and 8. However, in other states, posture of the surgical machine 200 or position and posture of the surgical machine 200 may be changed.

With reference to FIGS. 7 and 8, after moving the surgical machine 200 to the second position and changing the marker module 300 to the second posture, a coordinate signal regarding the marker 310 of the marker module 300 and generated by the sensing element 110 and a displacement and/or angle signal regarding the marker module 300 and generated by the displacement and/or angle sensing element 120 are sent to the processor 130. The position of the surgical machine 200 and the posture of the marker module 300 are both changed in the third state, as a result, the information in the coordinate signal regarding the moved marker 310 is different to that in the original coordinate signal, and the information in the displacement and/or angle signal regarding the moved marker module 300 is different to that in the original displacement and/or angle signal. While the coordinate signal is different to the original coordinate signal, a transformation matrix is created by the processor 130 according to the information in the displacement and/or angle signal regarding the moved marker module 300.

With reference to FIGS. 7 and 8, the surgical machine 200 and the marker module 300 are both moved in the third state such that a position and posture information obtained using the transformation matrix with the information in the coordinate signal is different to the original position and posture information. An update of the original position and posture information is required.

The position and posture information is obtained using the coordinate signal and the transformation matrix created based on the displacement and/or angle signal and is provided to be compared with the original position and posture information to determine whether need to update the original position and posture information. If position and/or posture of the surgical machine 200 and/or posture of the marker module 300 is changed during surgery, it can know the position and posture information of the surgical machine 200 is the same as the original position and posture information or not by the system 100 of the present invention. Consequently, accuracy and success rate of surgery can be enhanced by increasing accuracy of surgery navigation.

While this invention has been particularly illustrated and described in detail with respect to the preferred embodiments thereof, it will be clearly understood by those skilled in the art that is not limited to the specific features shown and described and various modified and changed in form and details may be made without departing from the scope of the claims.

What is claimed is:

1. A system for position and posture detection configured to determine whether to update an original position and posture information of a surgical machine stored in a surgery navigation system after moving or changing posture of the surgical machine and/or a marker module mounted on the surgical machine, the system comprising:
   a sensing element configured to sense a marker of the marker module and generate a coordinate signal;
   a displacement and/or angle sensing element configured to sense the marker module and generate a displacement and/or angle signal; and
   a processor configured to receive the coordinate signal and the displacement and/or angle signal, wherein the processor is configured to create a transformation matrix according to the displacement and/or angle signal while the coordinate signal is different to an original coordinate signal of the marker and generate a position and posture information of the surgical machine using the transformation matrix and the coordinate signal, the position and posture information is configured to be used to determine whether to update the original position and posture information.

2. The system in accordance with claim 1, wherein the marker module includes a linkage mechanism, and the marker is disposed on the linkage mechanism.

3. The system in accordance with claim 2, wherein the displacement and/or angle sensing element is disposed between two links of the linkage mechanism.

4. A method for position and posture detection configured to determine whether to update an original position and posture information of a surgical machine stored in a surgery navigation system after moving or changing posture of the surgical machine and/or a marker module mounted on the surgical machine, the method comprising:
   sensing a marker of the marker module to generate a coordinate signal using a sensing element;
   sensing the marker module to generate a displacement and/or angle signal using a displacement and/or angle sensing element; and
   receiving the coordinate signal and the displacement and/or angle signal using a processor, wherein the processor is configured to create a transformation matrix according to the displacement and/or angle signal while the coordinate signal is different to an original coordinate signal of the marker and generate a position and posture information of the surgical machine using the transformation matrix and the coordinate signal, the position and posture information is configured to be used to determine whether to update the original position and posture information.

5. The method in accordance with claim 4, wherein while the displacement and/or angle signal is different to an original displacement and/or angle signal of the marker module and the position and posture information generated by the processor using the transformation matrix and the coordinate signal is identical to the original position and posture information, the original position and posture information is configured to be not updated.

6. The method in accordance with claim 5, wherein while the displacement and/or angle signal is identical to the original displacement and/or angle signal of the marker module and the position and posture information generated by the processor using the transformation matrix and the coordinate signal is different to the original position and posture information, the original position and posture information is configured to be updated.

7. The method in accordance with claim 6, wherein while the displacement and/or angle signal is different to the original displacement and/or angle signal of the marker module and the position and posture information generated by the processor using the transformation matrix and the coordinate signal is different to the original position and posture information, the original position and posture information is configured to be updated.

8. The method in accordance with claim 5, wherein while the displacement and/or angle signal is different to the original displacement and/or angle signal of the marker module and the position and posture information generated by the processor using the transformation matrix and the coordinate signal is different to the original position and posture information, the original position and posture information is configured to be updated.

9. The method in accordance with claim 4, wherein while the displacement and/or angle signal is identical to an original displacement and/or angle signal of the marker module and the position and posture information generated by the processor using the transformation matrix and the coordinate signal is different to the original position and posture information, the original position and posture information is configured to be updated.

10. The method in accordance with claim 9, wherein while the displacement and/or angle signal is different to the original displacement and/or angle signal of the marker module and the position and posture information generated by the processor using the transformation matrix and the coordinate signal is different to the original position and posture information, the original position and posture information is configured to be updated.

11. The method in accordance with claim 4, wherein while the displacement and/or angle signal is different to an original displacement and/or angle signal of the marker module and the position and posture information generated by the processor using the transformation matrix and the coordinate signal is different to the original position and posture information, the original position and posture information is configured to be updated.

12. The method in accordance with claim 4, wherein the marker module includes a linkage mechanism, and the marker is disposed on the linkage mechanism.

13. The method in accordance with claim 12, wherein the displacement and/or angle sensing element is disposed between two links of the linkage mechanism.

* * * * *